United States Patent
Iwanowicz et al.

(10) Patent No.: US 11,701,473 B2
(45) Date of Patent: Jul. 18, 2023

(54) REUSABLE INJECTION PENS

(71) Applicant: Medtronic MiniMed, Inc., Northridge, CA (US)

(72) Inventors: Martin W. Iwanowicz, San Diego, CA (US); Jack Pryor, Ladera Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 195 days.

(21) Appl. No.: 17/355,555

(22) Filed: Jun. 23, 2021

(65) Prior Publication Data

US 2022/0409818 A1 Dec. 29, 2022

(51) Int. Cl.
*A61M 5/315* (2006.01)
*A61M 5/20* (2006.01)

(52) U.S. Cl.
CPC .......... *A61M 5/31528* (2013.01); *A61M 5/20* (2013.01); *A61M 5/31581* (2013.01); *A61M 2005/3152* (2013.01); *A61M 2005/31588* (2013.01); *A61M 2205/50* (2013.01)

(58) Field of Classification Search
CPC ................ A61M 5/31528; A61M 5/20; A61M 5/31581; A61M 2005/3152; A61M 2005/31588
See application file for complete search history.

(56) References Cited

U.S. PATENT DOCUMENTS

| | | | |
|---|---|---|---|
| 4,498,904 A | 2/1985 | Turner et al. | |
| 4,515,584 A | 5/1985 | Abe et al. | |
| 4,950,216 A | 8/1990 | Weder | |
| 4,973,318 A | 11/1990 | Holm et al. | |
| 4,988,660 A | 1/1991 | Campbell | |
| 5,279,586 A | 1/1994 | Balkwill | |
| 5,626,566 A | 5/1997 | Petersen et al. | |
| 5,681,285 A | 10/1997 | Ford et al. | |
| 5,822,715 A | 10/1998 | Worthington et al. | |
| 5,925,021 A | 7/1999 | Castellano et al. | |
| 5,984,900 A | 11/1999 | Mikkelsen | |
| 6,004,297 A | 12/1999 | Steenfeldt-Jensen et al. | |
| 6,042,571 A | 3/2000 | Hjertman et al. | |
| 6,235,004 B1 | 5/2001 | Steenfeldt-Jensen et al. | |
| 6,302,855 B1 | 10/2001 | Lav et al. | |
| 6,482,185 B1 | 11/2002 | Hartmann | |
| 6,817,986 B2 | 11/2004 | Slate et al. | |
| 7,591,801 B2 | 9/2009 | Brauker et al. | |

(Continued)

FOREIGN PATENT DOCUMENTS

EP 0298067 A1 1/1989
EP 0513128 A1 11/1992
(Continued)

OTHER PUBLICATIONS

Extended European Search Report issued in corresponding application EP 22179824.2 dated Nov. 4, 2022 (7 pages).

*Primary Examiner* — Dung T Ulsh
(74) *Attorney, Agent, or Firm* — Carter, DeLuca & Farrell LLP

(57) ABSTRACT

A medicine injection pen includes a rotatable drive member and a rotary encoder associated with the drive member. The rotary encoder is configured to determine an amount of liquid medicine dispensed based on a rotational orientation of the drive member.

20 Claims, 4 Drawing Sheets

(56) References Cited

U.S. PATENT DOCUMENTS

| | | |
|---|---|---|
| 7,905,833 B2 | 3/2011 | Brister et al. |
| 7,955,303 B2 | 6/2011 | Burren et al. |
| 7,976,492 B2 | 7/2011 | Brauker et al. |
| 8,221,356 B2 | 7/2012 | Enggaard et al. |
| 8,229,535 B2 | 7/2012 | Mensinger et al. |
| 8,231,531 B2 | 7/2012 | Brister et al. |
| RE43,834 E | 11/2012 | Steenfeldt-Jensen et al. |
| 8,460,231 B2 | 6/2013 | Brauker et al. |
| 8,565,848 B2 | 10/2013 | Brister et al. |
| D694,252 S | 11/2013 | Helm |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,750,955 B2 | 6/2014 | Mensinger et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| D727,928 S | 4/2015 | Allison et al. |
| 9,020,572 B2 | 4/2015 | Mensinger et al. |
| 9,050,413 B2 | 6/2015 | Brauker et al. |
| D738,385 S | 9/2015 | Lim et al. |
| 9,143,569 B2 | 9/2015 | Mensinger et al. |
| 9,155,843 B2 | 10/2015 | Brauker et al. |
| D747,333 S | 1/2016 | Supino et al. |
| D748,101 S | 1/2016 | Bang et al. |
| D748,126 S | 1/2016 | Sarukkai et al. |
| D749,103 S | 2/2016 | Song |
| D753,685 S | 4/2016 | Zimmerman et al. |
| D754,689 S | 4/2016 | Lee |
| D759,684 S | 6/2016 | Bijlani et al. |
| D761,280 S | 7/2016 | Chung et al. |
| D763,308 S | 8/2016 | Wang et al. |
| D766,958 S | 9/2016 | Salazar Cardozo et al. |
| 9,446,194 B2 | 9/2016 | Kamath et al. |
| D777,760 S | 1/2017 | Zhao et al. |
| D781,890 S | 3/2017 | Gathman et al. |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| D786,273 S | 5/2017 | Herman et al. |
| 9,672,328 B2 | 6/2017 | Saint |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| D797,760 S | 9/2017 | Tsujimura et al. |
| D798,312 S | 9/2017 | Tsujimura et al. |
| 9,775,543 B2 | 10/2017 | Brister et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| 9,937,293 B2 | 4/2018 | Brauker et al. |
| D819,043 S | 5/2018 | Yamaura et al. |
| D820,297 S | 6/2018 | Gardner et al. |
| 9,996,668 B2 | 6/2018 | Reihman et al. |
| D831,049 S | 10/2018 | Agarwal et al. |
| D831,684 S | 10/2018 | Ghosh |
| D832,292 S | 10/2018 | Hu et al. |
| D832,870 S | 11/2018 | Hu |
| D833,469 S | 11/2018 | Coleman et al. |
| D835,118 S | 12/2018 | Lee et al. |
| D837,807 S | 1/2019 | Baber et al. |
| D838,734 S | 1/2019 | Kruse et al. |
| 10,169,539 B2 | 1/2019 | Reihman et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Cheney et al. |
| D849,757 S | 5/2019 | Jing et al. |
| 10,278,580 B2 | 5/2019 | Brister et al. |
| 10,898,653 B2 | 1/2021 | Saint et al. |
| 2003/0065536 A1 | 4/2003 | Hansen et al. |
| 2004/0039255 A1 | 2/2004 | Simonsen et al. |
| 2005/0038674 A1 | 2/2005 | Braig et al. |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0038044 A1 | 2/2007 | Dobbles et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2009/0036771 A1 | 2/2009 | Fago et al. |
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |
| 2009/0209938 A1 | 8/2009 | Aalto-Setala |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0185075 A1 | 7/2010 | Brister et al. |
| 2010/0261987 A1 | 10/2010 | Kamath et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0264033 A1 | 10/2011 | Jensen et al. |
| 2011/0270158 A1 | 11/2011 | Brauker et al. |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0171938 A1 | 7/2013 | Mears et al. |
| 2013/0184996 A1 | 7/2013 | Zivitz et al. |
| 2013/0197445 A1 | 8/2013 | Schabbach et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0074041 A1 | 3/2014 | Pedersen et al. |
| 2014/0113856 A1 | 4/2014 | Pohl et al. |
| 2014/0114158 A1 | 4/2014 | Brister et al. |
| 2014/0114161 A1 | 4/2014 | Kamath et al. |
| 2014/0257065 A1 | 9/2014 | Walsh |
| 2014/0276531 A1 | 9/2014 | Walsh |
| 2014/0288494 A1 | 9/2014 | Brister et al. |
| 2014/0330206 A1* | 11/2014 | Moore .............. A61M 5/14216 604/152 |
| 2015/0073337 A1 | 3/2015 | Saint et al. |

(56) References Cited

U.S. PATENT DOCUMENTS

| | | |
|---|---|---|
| 2015/0202377 A1 | 7/2015 | Haupt |
| 2015/0351683 A1 | 12/2015 | Brauker et al. |
| 2015/0359965 A1 | 12/2015 | O'Connor et al. |
| 2016/0012205 A1 | 1/2016 | Saint |
| 2016/0030683 A1 | 2/2016 | Taylor |
| 2016/0066843 A1 | 3/2016 | Mensinger et al. |
| 2016/0081632 A1 | 3/2016 | Kamath et al. |
| 2016/0101232 A1 | 4/2016 | Kamath et al. |
| 2017/0068799 A1 | 3/2017 | Mensinger et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0185283 A1 | 6/2017 | Bhavaraju et al. |
| 2017/0185284 A1 | 6/2017 | Bhavaraju |
| 2017/0189625 A1 | 7/2017 | Cirillo et al. |
| 2017/0270276 A1 | 9/2017 | Saint et al. |
| 2017/0286194 A1 | 10/2017 | Morris et al. |
| 2017/0286614 A1 | 10/2017 | Morris et al. |
| 2017/0366617 A1 | 12/2017 | Mensinger et al. |
| 2017/0367627 A1 | 12/2017 | Brister et al. |
| 2018/0185587 A1 | 7/2018 | Brauker et al. |
| 2018/0303417 A1 | 10/2018 | Mensinger et al. |
| 2018/0353698 A1 | 12/2018 | Saint et al. |
| 2019/0015020 A1 | 1/2019 | Brister et al. |
| 2019/0035500 A1 | 1/2019 | Saint et al. |
| 2019/0091412 A1* | 3/2019 | Gabriel ............. A61M 5/31546 |
| 2019/0125224 A1 | 5/2019 | Kamath et al. |
| 2019/0132801 A1 | 5/2019 | Kamath et al. |
| 2019/0173885 A1 | 6/2019 | Kamath et al. |
| 2021/0046246 A9* | 2/2021 | Saint ....................... G08B 21/02 |
| 2021/0299349 A1* | 9/2021 | Tada ...................... H02N 2/145 |
| 2023/0001095 A1* | 1/2023 | Antonelli ................ A61M 5/20 |

FOREIGN PATENT DOCUMENTS

| | | |
|---|---|---|
| EP | 0927057 A1 | 7/1999 |
| EP | 2572740 A1 | 3/2013 |
| WO | 9638190 A1 | 12/1996 |
| WO | 2010052275 A2 | 5/2010 |
| WO | 2011041007 A1 | 4/2011 |
| WO | 2012046199 A1 | 4/2012 |
| WO | 2013053695 A1 | 4/2013 |
| WO | 2014128157 A1 | 8/2014 |
| WO | 2015047870 A1 | 4/2015 |
| WO | 2015169814 A1 | 11/2015 |
| WO | 2015185686 A1 | 12/2015 |
| WO | 2016071912 A1 | 5/2016 |
| WO | 2017132577 A1 | 8/2017 |
| WO | 2018009509 A2 | 1/2018 |

* cited by examiner

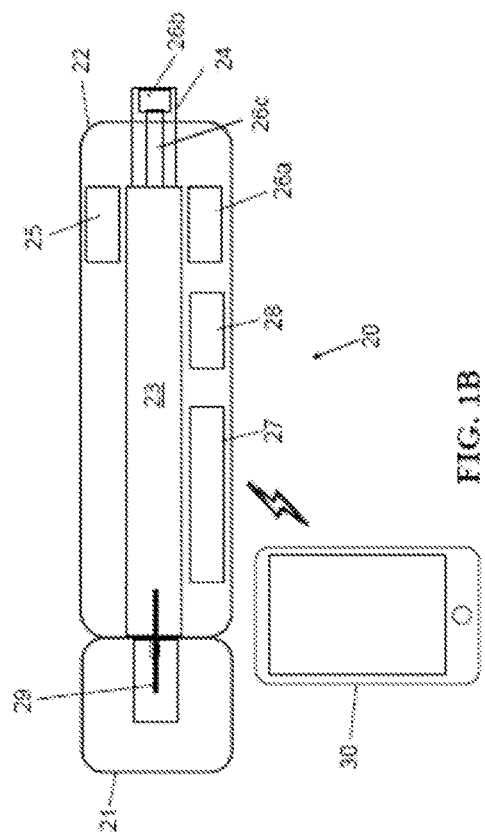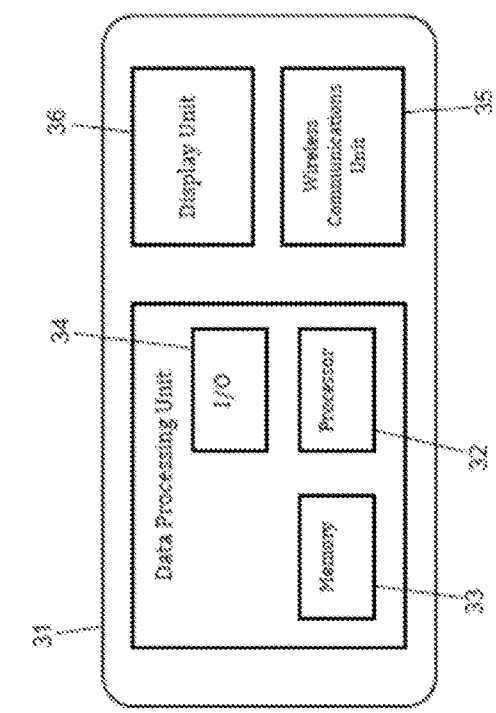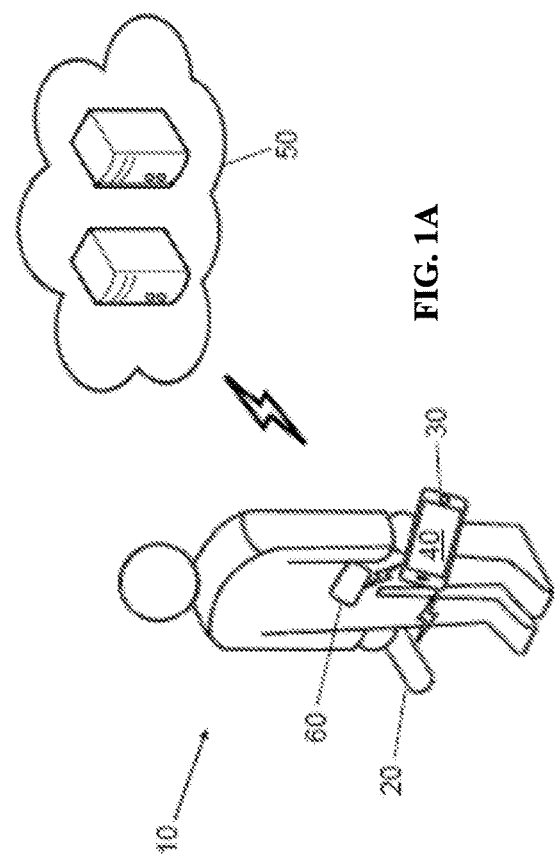
FIG. 1B
FIG. 1C
FIG. 1A

REUSABLE INJECTION PENS

FIELD

The present disclosure relates to medicine administration and tracking and, more specifically, to reusable injection pens with replaceable cartridges for medicine administration and tracking.

BACKGROUND

Diabetes mellitus ("diabetes") is a metabolic disease associated with high blood sugar due to insufficient production or use of insulin by the body. Diabetes affects hundreds of millions of people and is among the leading causes of death globally. Diabetes has been categorized into three types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. Gestational diabetes can occur during pregnancy when a pregnant woman develops a high blood glucose level. Gestational diabetes often resolves after pregnancy; however, in some cases, gestational diabetes develops into type 2 diabetes.

Various diseases and medical conditions, such as diabetes, require a user to self-administer doses of medicine. When administering a liquid medicine by injection, for example, the appropriate dose amount is set and then dispensed by the user, e.g., using a syringe, a medicine delivery pen, or a pump. Regardless of the particular device utilized for injecting the liquid medicine, it is important to accurately track the medicine dosed, particularly for managing lifelong or chronic conditions like diabetes.

SUMMARY

Provided in accordance with aspects of the present disclosure is a medicine injection pen including a body, a drive member, a rotary encoder, and a gear set. The drive member is disposed within the body and configured to rotate in a first rotational direction relative to the body from a first position to a second position to dispense liquid medicine. The drive member is configured to rotate in a second rotational direction from the second position to the first position to reset the drive member. The rotary encoder includes a first part rotationally fixed relative to the body, and a second part configured to rotate with movement of the drive member to enable determination of an amount of liquid medicine dispensed based on a rotation of the second part relative to the first part. The gear set is operably coupled to the second part of the rotary encoder. The second part is configured to rotate freely relative to the gear set during movement of the drive member in the first rotational direction and to engage the gear set during movement of the drive member in the second rotational direction.

In aspects, the gear set may be a planetary gear set and includes a sun gear and a plurality of planet gears in meshing engagement with the sun gear. The second part may be configured to rotate about the sun gear with the planet gears in the second rotational direction.

In aspects, the sun gear may be configured to rotate with the drive member in the second rotational direction as the drive member moves from the second position to the first position.

In aspects, the second part of the rotary encoder may be configured to rotate with the drive member in the first rotational direction at the same rate as the drive member as the drive member moves from the first position to the second position. The second part may be configured to rotate with the planet gears via the sun gear in the second rotational direction at a lesser rate than the drive member as the drive member moves from the second position to the first position.

In aspects, the drive member and the second part may be configured to be rotated by a motor.

In aspects, the medicine injection pen may further include a processor in communication with the motor. The processor may be configured to automatically control the motor to rotate the drive member in the second rotational direction upon the drive member moving to a predetermined position.

In aspects, the drive member may be a drive screw configured to rotate and translate relative to the body to urge a piston to slide to dispense the liquid medicine.

In aspects, the rotary encoder may be configured to sense rotation of the drive screw to enable determination of the amount of the liquid medicine dispensed.

In aspects, the medicine injection pen may further include an electronics unit configured to determine the amount of the liquid medicine dispensed based on the sensed rotation.

In aspects, the medicine injection pen may further include a cartridge housing releasably engageable with the body and configured to retain a medicine cartridge therein. The medicine cartridge may be configured to retain the liquid medicine therein. The medicine cartridge may include a piston configured to slide within the medicine cartridge. The drive member may be configured to move relative to the body upon actuation thereof to urge the piston to slide within the medicine cartridge to thereby dispense at least some of the liquid medicine through a dispensing end of the medicine cartridge.

In accordance with another aspect of the disclosure, a medicine injection pen is provided and includes a body, a drive member disposed within the body, a rotary encoder, and a gear set. The drive member is configured to rotate in a first rotational direction relative to the body from a first position to a second position to dispense liquid medicine. The drive member is configured to rotate in a second rotational direction from the second position to the first position to reset the drive member. The rotary encoder includes a first part rotationally fixed relative to the body, and a second part configured to rotate with movement of the drive member to enable determination of an amount of liquid medicine dispensed based on a rotational orientation of the second part relative to the first part. The gear set is operably coupled to the second part of the rotary encoder. The second part of the rotary encoder is configured to rotate with the drive member in the first rotational direction at the same rate as the drive member as the drive member moves from the first position to the second position. The second part is configured to rotate with the gear set in the second rotational direction at a lesser rate than the drive member as the drive member moves from the second position to the first position.

BRIEF DESCRIPTION OF DRAWINGS

FIG. 1A is a schematic illustration of a medicine administration and tracking system provided in accordance with the present disclosure including a medicine injection pen, a computing device, and, in aspects, a sensor device and/or a data processing system;

FIG. 1B is a block diagram of the medicine injection pen of the system of FIG. 1A;

FIG. 1C is a block diagram of the computing device of the system of FIG. 1A;

DETAILED DESCRIPTION

Figure 2A:
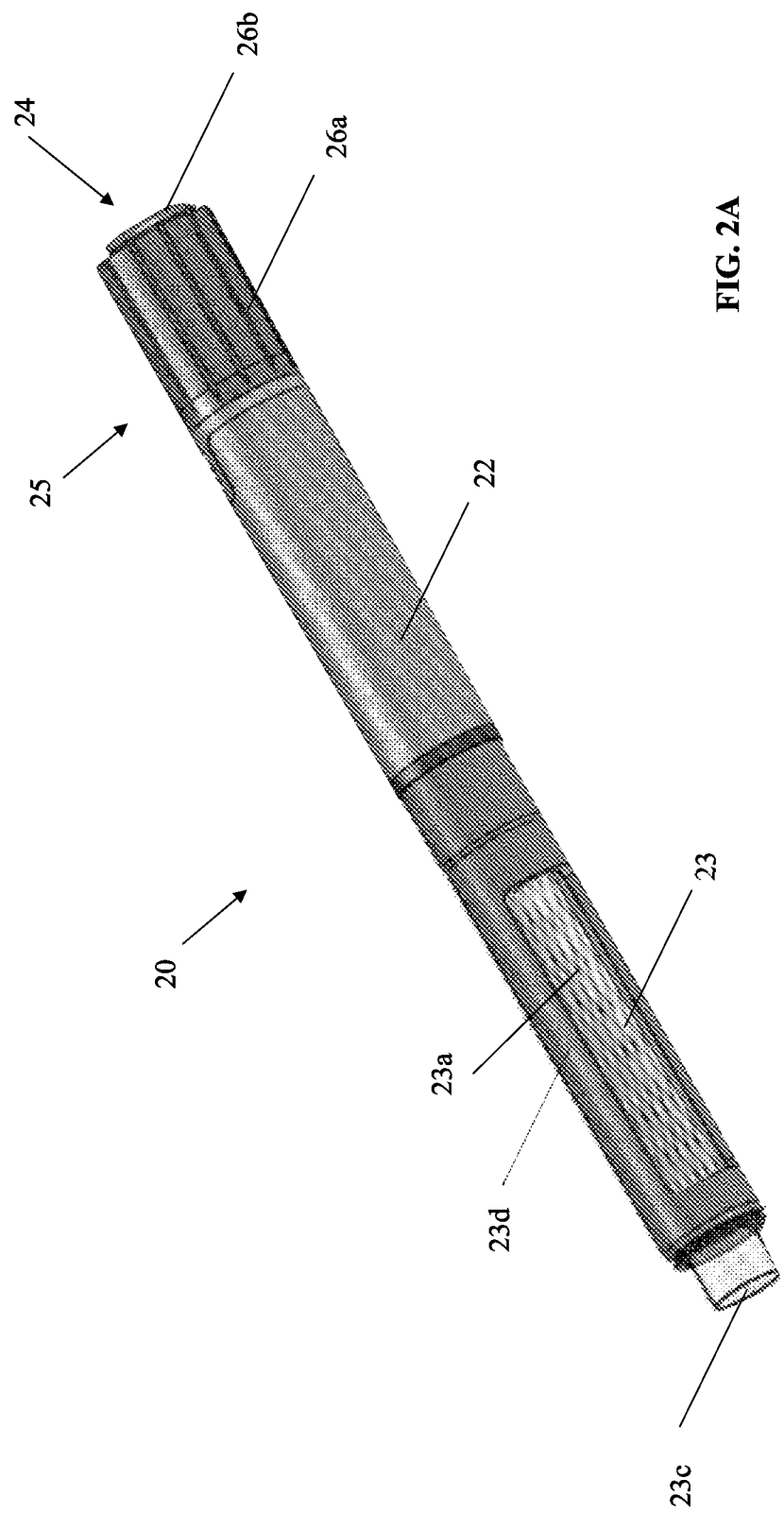
FIGS. 2A and 2B are perspective and longitudinal, cross-sectional views, respectively, of the medicine injection pen of FIG. 1B.

FIG. 1A illustrates a medicine administration and tracking system 10 provided in accordance with the present disclosure including a medicine injection pen 20 in wireless communication with a computing device 30 running a health management application 40 associated with pen 20 and/or other devices part of or connected to system 10. System 10, in aspects, further includes a data processing system 50 and/or a sensor device 60. While the reusable injection pens with replaceable cartridges of the present disclosure are detailed herein configured for use as medicine injection pen 20 of system 10 with respect to diabetes management, it is understood that the reusable injection pens of the present disclosure are also applicable to management of other diseases and medical conditions and/or for use with other medicine administration and tracking systems.

Medicine injection pen 20, described in greater detail below, is a reusable injection pen configured to removably receive a medicine cartridge, e.g., a cartridge of insulin, for injecting a selected dose of insulin into a patient and recording information concerning the injected dose of insulin, e.g., a dose amount and/or timestamp data associated with the dose.

Computing device 30 is detailed and illustrated herein as a smartphone, although any other suitable computing device may be provided such as, for example, a tablet, a wearable computing device (e.g., a smart watch, smart glasses, etc.), a laptop and/or desktop computer, a smart television, a network-based server computer, etc.

Health management application 40 is paired with pen 20, which may be a prescription-only medical device, via smartphone 30, although other suitable configurations are also contemplated. In aspects, the pairing of smartphone 30 with pen 20 at least partially unlocks health management application 40 to enable the user to utilize some or all features of health management application 40, e.g., according to the user's prescription. Thus, the act of pairing can unlock and enable the functionality of health management application 40 and/or system 10 (including pen 20), while health management application 40 (and/or system 10) may provide only limited features in the absence of pairing with pen 20.

Health management application 40 of smartphone 30, in aspects, can monitor and/or control functionalities of pen 20 and provide a dose calculator module and/or decision support module that can calculate and recommend a dose of medicine for the user to administer using pen 20. Health management application 40 provides a user interface, on the user interface of smartphone 30, to allow a user to manage health-related data. For example, health management application 40 can be configured to control some functionalities of pen 20 and/or to provide an interactive user interface to allow a user to manage settings of pen 20 and/or settings for smartphone 30 that can affect the functionality of system 10 (FIG. 1A). Smartphone 30 can additionally or alternatively be used to obtain, process, and/or display contextual data that can be used to relate to the health condition of the user, including the condition for which pen 20 is used to treat. For example, smartphone 30 may be operable to track the location of the user; physical activity of the user including step count, movement distance and/or intensity, estimated calories burned, and/or activity duration; and/or interaction pattern of the user with smartphone 30. In aspects, health management application 40 can aggregate and process the contextual data to generate decision support outputs, e.g., on the user interface, to guide and aid the user in monitoring their condition, using pen 20, and/or managing their behavior to promote treatment and better health outcomes.

In aspects, system 10 further includes a data processing system 50 in communication with pen 20 and/or smartphone 30. Data processing system 50 can include one or more computing devices in a computer system and/or communication network accessible via the internet, e.g., including servers and/or databases in the cloud. System 10 can additionally or alternatively include sensor device 60 to monitor one or more health metrics and/or physiological parameters of the user. Examples of health metric and physiological parameter data monitored by sensor device 60 include analytes (e.g., glucose), heart rate, blood pressure, user movement, temperature, etc. Sensor device 60 may be a wearable sensor device such as a continuous glucose monitor (CGM) to obtain transcutaneous or blood glucose measurements that are processed to produce continuous glucose values. For example, the CGM can include a glucose processing module implemented on a stand-alone display device and/or implemented on smartphone 30, which processes, stores, and displays the continuous glucose values for the user. Such continuous glucose values can be utilized by health management application 40, for example, for displaying health data, in dose calculation and/or decision support, etc.

With reference to FIG. 1B, pen 20 includes a cap 21 configured to protect a medicine dispensing element (e.g., a needle 29) and a body 22 configured to contain a replaceable medicine cartridge 23, e.g., an insulin cartridge. Pen 20 further includes a dose dispensing mechanism 24 to dispense (e.g., deliver) medicine contained in medicine cartridge 23 out of pen 20 (e.g., through needle 29); a dose setting mechanism 25 to enable the selection and/or setting of a dose of medicine to be dispensed; an operations monitoring mechanism 28 (e.g., including one or more switches, sensors (electrical, optical, acoustic, magnetic, etc.), encoders, etc.) to qualitatively determine that pen 20 is being operated and/or to monitor the operation of pen 20 (e.g., to quantitatively determine an amount of medicine set and/or dosed); and an electronics unit 27 that can include a processor, a memory, a transceiver, and a battery or other suitable power source.

In aspects, in order to operate pen 20, the user first sets e.g., dials, a dose using a dose knob 26a of dose setting mechanism 25. For example, the dose may be adjusted up or down to achieve a desired dose amount prior to administration of the dose by rotating dose knob 26a in an appropriate direction. Once the appropriate dose has been set, the user applies a force against a dose dispensing button 26b of dose setting mechanism 25 to begin dispensing. More specifically, to begin dispensing, the user presses against the portion of dose dispensing button 26b that protrudes from body 22 of pen 20 to thereby drive a driving element 26c, e.g., a drive screw 26c, of dose dispensing mechanism 24 against an abutment, e.g., piston 23b (FIG. 2B), of medicine cartridge 23 to dispense an amount of medicine from cartridge 23 through needle 29 into the user in accordance with the dose amount set by dose setting mechanism 25, e.g., dose knob 26a, during setting.

Operations monitoring mechanism 28 of pen 20 senses movement of a rotating and/or translating driving component (e.g., drive screw 26c (see also FIG. 2B)) of dose dispensing mechanism 24. Operations monitoring mechanism 28 may include one or more switches, sensors, and/or encoders for this purpose. More specifically, any suitable switch(es), sensor(s), and/or encoder(s) may be utilized to sense rotary and/or linear movement. Non-limiting examples of such include rotary and linear encoders, Hall effect and other magnetic-based sensors, linearly variable displacement transducers, optical sensors, etc. With respect to an encoder, for example, the encoder can be configured to sense the rotation of drive screw 26c (FIG. 2B) that, in turn, translates to dispense medicine; thus, by sensing rotation of drive screw 26c (FIG. 2B), the translational movement of drive screw 26c can be readily determined. Movement of the encoder may be detected as data processed by the processor of electronics unit 27 of pen 20, from which the amount of medicine dosed can be determined.

In aspects, the processor of electronics unit 27 of pen 20 can store the dose along with a timestamp for that dose and/or any other information associated with the dose. In aspects, the transceiver of electronics unit 27 enables pen 20 to transmit the dose and related information to smartphone 30. In such aspects, once the dose is transmitted, the dose data and any related information associated with that particular transmitted dose is marked in the memory of electronics unit 27 of pen 20 as transmitted. If the dose is not yet transmitted to smartphone 30 such as, for example, because no connection between the pen 20 and smartphone 30 is available, then the dose and associated data can be saved and transmitted the next time a successful communication link between pen 20 and smartphone 30 is established.

The timestamp may be the current time or a time from a count-up timer. When the dose and associated information is communicated to health management application 40 running on smartphone 30, the timestamp and/or "time-since-dose" parameter (as determined by the count-up timer) is transmitted by pen 20 and received by smartphone 30 for storage in memory 33 of data processing unit 31 of the smartphone 30 (see FIG. 1C). Where a count-up timer is utilized, the time of the dose can be determined without pen 20 having to know the current time, which can simplify operation and setup of pen 20. That is, health management application 40 can determined the time of dose based on the current time and the value returned from the count-up timer.

Dose dispensing mechanism 24 of pen 20 can include a manually powered mechanism, a motorized mechanism, or an assisted mechanism (e.g., a mechanism that operates partly on manual power and partly on motorized power). Regardless of the particular configuration of the dose dispensing mechanism 24, as noted above, when a force (e.g., a manual force, electrically-powered motor force, or combinations thereof) is applied to drive screw 26c of dose dispensing mechanism 24, drive screw 26c in turn provides a force to urge medicine from medicine cartridge 23 to deliver the set or dialed dose. In aspects, dose dispensing mechanism 24 can be operated such that rotation and/or translation of the driving element, e.g., drive screw 26c, is facilitated by a variable tension spring or a variable speed motor to inject the dose over a specific time frame (e.g., 1 s, 5 s, etc.) to help reduce the pain of dosing and/or for other purposes.

FIG. 1C illustrates smartphone 30 of system 10 (FIG. 1A) including a data processing unit 31, a wireless communications unit 35, and a display unit 36. Data processing unit 31 includes a processor 32 to process data, a memory 33 in communication with the processor 32 to store data, and an input/output unit (I/O) 34 to interface processor 32 and/or memory 33 to other modules, units, and/or devices of smartphone 30 and/or external devices. Processor 32 can include a central processing unit (CPU) or a microcontroller unit (MCU). Memory 33 can include and store processor-executable code, which when executed by processor 32, configures the data processing unit 31 to perform various operations, e.g., such as receiving information, commands, and/or data, processing information and data, and transmitting or providing information/data to another device. In aspects, data processing unit 31 can transmit raw or processed data to data processing system 50 (FIG. 1A). To support various functions of data processing unit 31, memory 33 can store information and data, such as instructions, software, values, images, and other data processed or referenced by processor 32. For example, various types of Random Access Memory (RAM) devices, Read Only Memory (ROM) devices, Flash Memory devices, and other suitable storage media can be used to implement storage functions of memory 33. I/O 34 of data processing unit 31 can interface data processing unit 31 with wireless communications unit 35 to utilize various types of wired or wireless interfaces compatible with typical data communication standards, for example, which can be used in communications of data processing unit 31 with other devices such as pen 20, via a wireless transmitter/receiver (Tx/Rx), e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. I/O 34 of data processing unit 31 can also interface with other external interfaces, sources of data storage, and/or visual or audio display devices, etc. to retrieve and transfer data and information that can be processed by processor 32, stored in memory 33, and/or exhibited on an output unit of smartphone 30 and/or an external device. For example, display unit 36 of smartphone 30 can be configured to be in data communication with data processing unit 31, e.g., via I/O 34, to provide a visual display, an audio display, and/or other sensory display that produces the user interface of the health management application 40 (FIG. 1A). In some examples, display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Once smartphone 30 receives the dose and related information (e.g., which can include time information, dose setting, and/or dose dispensing information, and other information about pen 20 and/or the environment as it relates to a dosing event), smartphone 30 stores the dose related information in memory 33, e.g., which can be included among a list of doses or dosing events. In aspects, via the user interface associated with health management application 40, smartphone 30 allows the user to browse a list of previous doses, to view an estimate of current medicine active in the patient's body (medicine on board, e.g., insulin on boar) based on calculations performed by health management application 40, and/or to utilize a dose calculation module to assist the patient regarding dose setting information on the size of the next dose(s) to be delivered. For example, the patient may enter carbohydrates to be eaten and current blood sugar (which alternatively may be obtained directly from sensor device 60 (FIG. 1A)), and health management application 40 may already know insulin on board. Using these parameters, a suggested medicine dose (e.g., a recommended insulin dose), calculated by the dose determination module, may be determined. In aspects, smartphone 30 can also allow the user to manually enter dose data, e.g., boluses, which may be useful if the battery in pen 20 has been depleted or another medicine delivery device, e.g., a syringe, was utilized to dose.

Figure 2B:
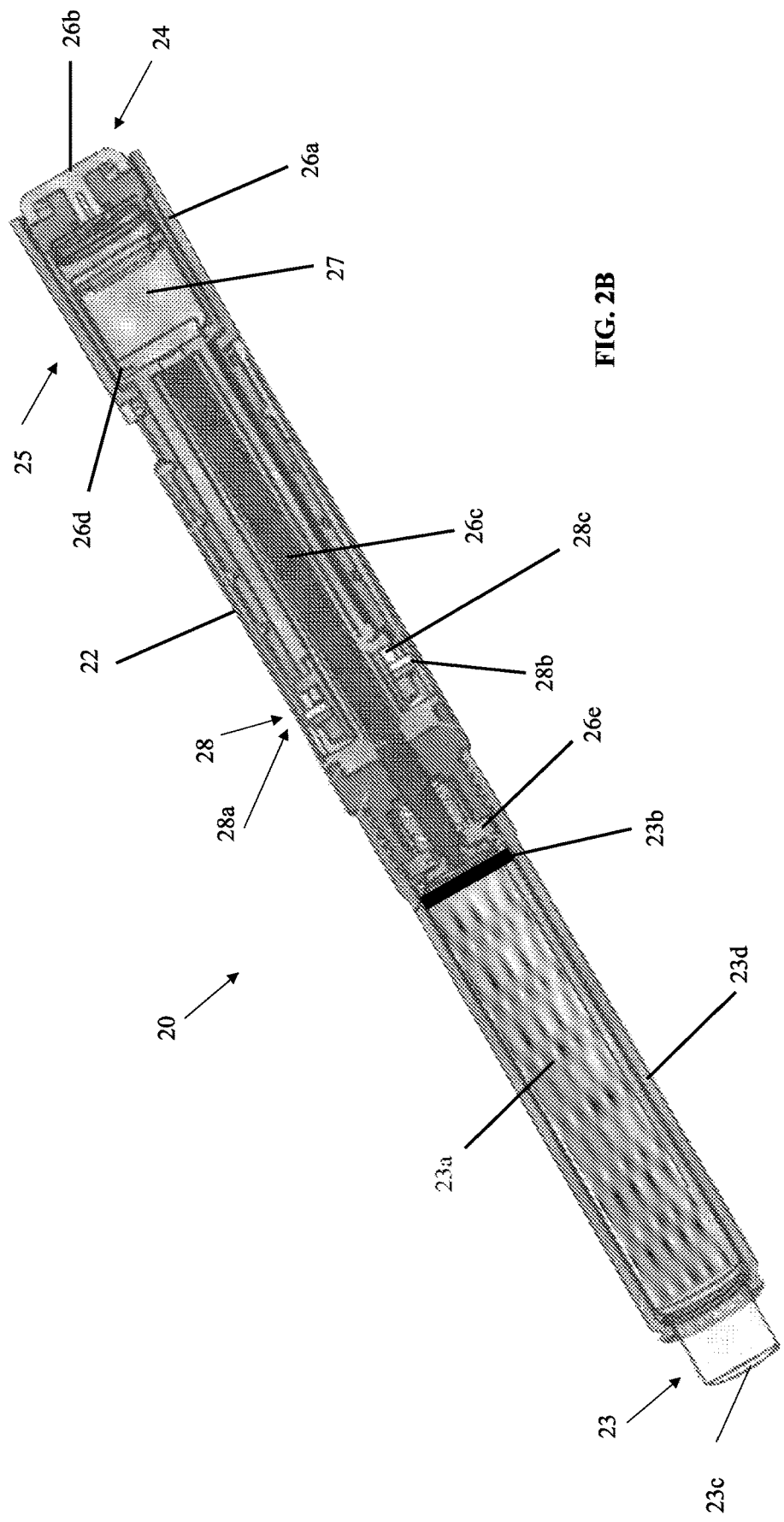
Figure 3A:
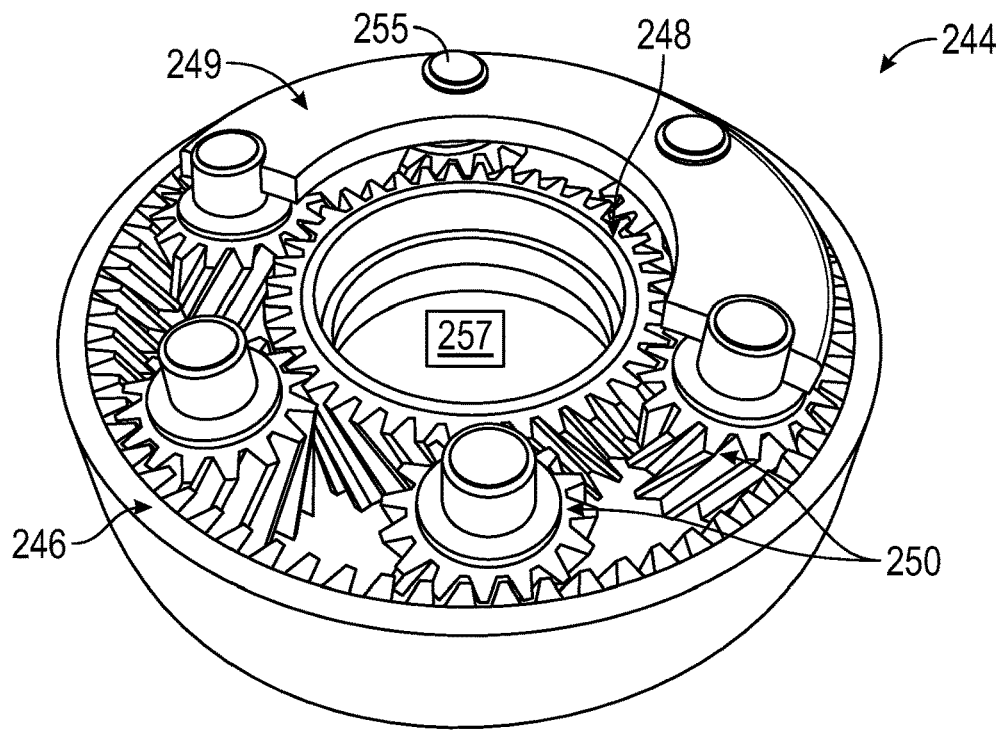
FIG. 3A is a perspective view illustrating a planetary gear set of the medicine injection pen of FIGS. 2A and 2B.
Figure 3B:
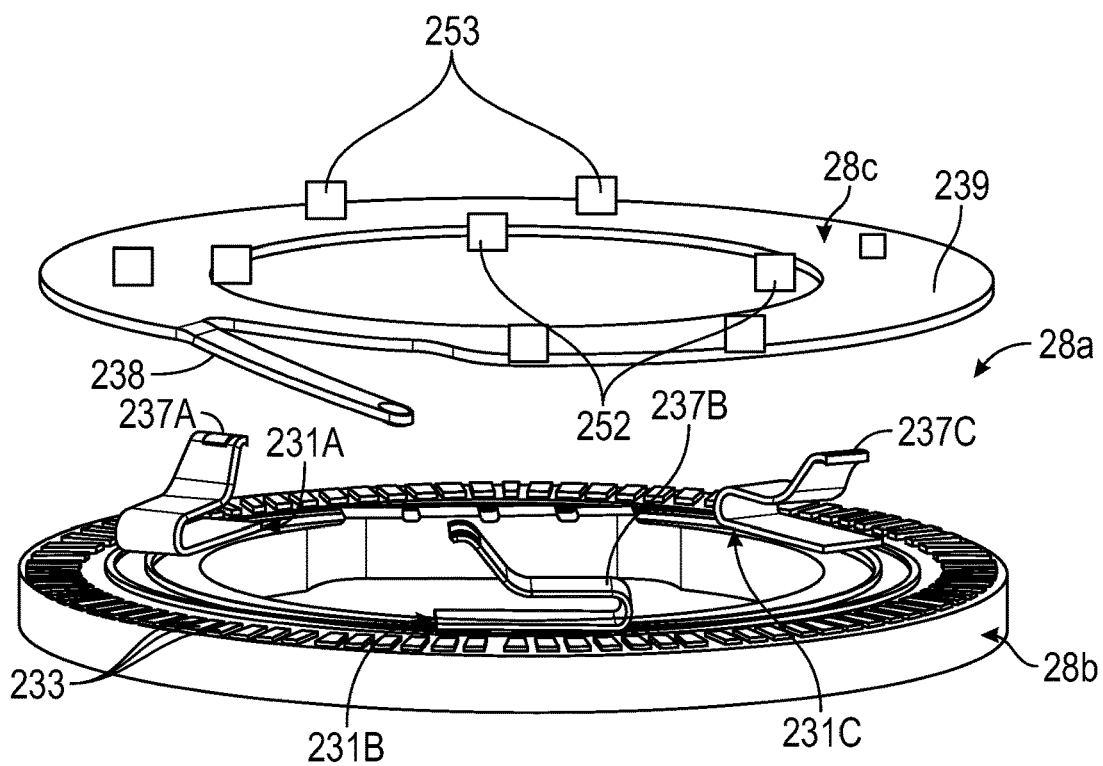
FIG. 3B is a perspective view, with parts separated, illustrating a rotary encoder of the medicine injection pen of FIGS. 2A and 2B.

Referring to FIGS. 2A and 2B, pen 20 and, in particular, the mechanical and hardware features thereof, is detailed, although other mechanical and hardware configurations of pen 20 are also contemplated. Pen 20 is shown configured as a reusable device for use with replaceable medicine cartridge 23 which, once emptied, can be replaced with another medicine cartridge 23 or refilled and reinstalled for subsequent use. Medicine cartridge 23 includes a vial body 23a defining an interior volume retaining a volume of medicine, e.g., insulin, therein, and a piston 23b sealingly and slidingly disposed within vial body 23a such that displacement of piston 23b within vial body 23a towards the dispensing end of vial body 23a forces medicine from the interior volume through dispensing opening 23c of cartridge 23 and into needle 29 (FIG. 1B) for injection into the user. As can be appreciated, the displacement distance of piston 23b is proportional to the amount of medicine dispensed.

Medicine cartridge 23 is held within a cartridge housing 23d of pen 20 and, in aspects, may be seated within a corresponding cartridge (not shown) positionable within cartridge housing 23d to enable use of various different medicine cartridges (e.g., of different size, shape, etc.) with pen 20. Cartridge housing 23d is releasably engageable with body 22 of pen 20, e.g., via threaded engagement, such that, when cartridge housing 23d is disengaged from body 22 of pen 20, medicine cartridge 23 can be removed and replaced and such that, when cartridge housing 23d is engaged with body 22 of pen 20 with a medicine cartridge 23 therein, medicine cartridge 23 is operably positioned relative to dose dispensing mechanism 24 of pen 20. However, other suitable configurations enabling removal and replacement of a medicine cartridge 23 are also contemplated.

Continuing with reference to FIGS. 2A and 2B, dose knob 26a of pen 20 may be coupled to body 22 of pen 20 in threaded engagement via corresponding threads defined on an exterior surface of a portion of dose knob 26a and an interior surface of a portion of body 22. In aspects, electronics unit 27 may reside within an electronics housing disposed or defined within dose knob 26a and be coupled thereto via a locking mechanism 26d (e.g., a catch-protrusion mechanism, a clutch, etc.) such that, when dose knob 26a is rotated into or out of body 22 to select or adjust the dose to be injected, electronics unit 27 remains stationary (e.g., wherein the locking mechanism 26d is in an unlocked state); however, when dispensing button 26b is actuated, locking mechanism 26d is engaged to lock electronics unit 27 and dose knob 26a to one another such that electronics unit 27 and dose knob 26a rotate together as they translate into body 22 upon actuation of dose dispensing mechanism 24 to inject the selected dose.

The rotation of the dose knob 26a (and electronics unit 27) during actuation drives (direct or indirect) rotation of drive screw 26c which rides within a nut 26e which is fixed to body 22 of pen 20. In this manner, rotation of drive screw 26c also results in translation of drive screw 26c (due to the pitched threading of drive screw 26c) towards medicine cartridge 23 to thereby drive piston 23b through vial body 23a to expel medicine from medicine cartridge 23 for injection into the user. The extent to which dose knob 26a extends from body 22 of pen 20 prior to actuation (which corresponds to the selected dose to be injected) defines the maximum amount of rotation of dose knob 26a and, thus, drive screw 26c during actuation; as such, the amount of medicine expelled from medicine cartridge 23 during actuation cannot exceed the selected dose amount.

With reference to FIGS. 2A, 2B, 3A, and 3B, operations monitoring mechanism 28 of pen 20 may include a rotary encoder 28a having a first part, such as, for example, an encoder pattern wheel 28b rotationally fixed relative to body 22 of pen 20, and a second part, such as, for example, an annular contact plate 28c rotationally fixed relative to drive screw 26c such that relative rotation between the first and second parts 28b, 28c (which, in turn, is indicative of rotation of drive screw 26c relative to body 22 during dose dispensing), can be sensed and, thus, from which an amount of medicine dispensed can be determined (due to the proportional relationship between rotation of drive screw 26c and translation of piston 23b). Alternatively or additionally, rotary encoder 28a may be configured to sense the amount of medicine dialed for dosing. Regardless of the particular type of encoder or other sensory components of operations monitoring mechanism 28, relative motion is measured and transmitted to electronics unit 27 for processing (e.g., determining an amount of medicine dispensed), storage (e.g., storing in memory the amount of medicine dispensed together with timestamp data) and/or transmission (e.g., transmitting the stored data to smartphone 30).

The encoder pattern wheel 28b may be coupled to the dose dispensing mechanism 24 and includes a plurality of segmented contact pads 233 arranged in an annular array around the encoder pattern wheel 28b. The encoder pattern wheel 28b further includes three ground pads 231A, 231B, 231C spaced around the inner periphery thereof. The ground pads 231A, 231B, 231C are configured to make ground connections to the annular contact plate 28c via spring connectors 237A, 237B, 237C. For additional details about the encoder pattern wheel 28b, reference may be made to U.S. Pat. No. 10,898,653, the entire contents of which are incorporated by reference herein.

The annular contact plate 28c includes a ring body 239 and an extension or leg 238 extending from an outer periphery of the ring body 239. The leg 238 of the annular contact plate 28c is configured to electromechanically interface with the segmented contact pads 233 during rotation of the annular contact plate 28c during rotation of the screw 26c to enable detection of an amount of relative rotation between annular contact plate 28c and encoder pattern wheel 28b and, thus, an amount of rotation of screw 26c, which corresponds to an amount of medicine dispensed, as detailed above. The annular contact plate 28c of the encoder 28a may be selectively coupled, e.g., via a one-way mechanism as detailed below, to a planetary gear set 244, which includes a ring gear 246, a sun gear 248, a plurality of planet gears 250 disposed between the ring gear 246 and the sun gear 248, and a carrier plate 249 fixed to the planet gears 250. The annular contact plate 28c is configured to be rotated by the carrier plate 249 relative to the ring gear 246 in only the second rotational direction, as will be described. Due to the gear ratio provided by the planetary gear set 244, manual rotation of the screw 26c to retract the screw 26c and reset the rotary encoder 28 is made easier and will occur at a slower rate, such as, for example, about ½ the speed, although other suitable gear ratios and corresponding speed attenuations are also contemplated.

In aspects, the sun gear 248 or the screw 26c may be operably coupled to a drive motor, such as, for example, a hollow core electric motor 257 (FIG. 3A) configured to be automatically actuated upon the electronics unit 27 sensing that the dose dispensing mechanism 24 has fully injected the selected dose, that screw 26c has reached a fully extended position, that cartridge 23 is empty, that cartridge 23 has been removed and/or replaced, and/or based on any other sensed or input data. The drive motor may retract screw 26c a pre-defined amount, to a pre-defined position, or in any other suitable manner In aspects, instead of a drive motor, the sun gear 248 may be fixed about the screw to rotate with the screw 26c. In use, a user may manually rotate the screw 26c back to a more-retracted or fully-retracted position. Rotation of screw 26c rotates the sun gear 248 to, in turn, rotate the annular contact plate 28c in the second rotational direction at a reduced speed such that frictional and other forces associated with rotation of annular contact plate 28c in the second rotational direction are reduced, thus facilitating the user's manual rotation of screw 26c.

With respect to a one-way mechanism, the annular contact plate 28c may include a first set of teeth or pawls 252 extending from an inner periphery thereof and a second set of teeth or pawls 253 extending from a surface thereof. In aspects, the screw 26c may include a plurality of teeth or a pawl (not shown) configured to engage the first set of pawls 252 of the annular contact plate 28c during rotation of the screw 26c in a first rotational direction corresponding to the direction to deploy or extend the screw 26c, e.g., to dispense medicine from cartridge 23. As such, the screw 26c and the annular contact plate 28c rotate with one another at a 1:1 rate of rotation when the screw 26c is rotating in the first rotational direction. When the screw 26c is rotated in the second rotational direction corresponding to the direction of rotation to retract/reset the screw 26c (whether motorized or manually), the screw 26c is free to pass over the pawls 252 of the annular contact plate 28c to allow rotation of the screw 26c relative to the annular contact plate 28c. The second set of pawls 253 of the annular contact plate 28c are configured to engage surface features 255 extending from the carrier plate 249 of the planetary gear set 244 when the carrier plate 249 rotates in the second rotational direction such that the planetary gear set 244 is coupled between the screw 26c and the annular contact plate 28c to attenuate the speed of rotation of annular contact plate 28c as compared to the rotational input to back-drive screw 26c.

In operation, the screw 26c is rotated either manually or by the motor in the first rotational direction to move the screw 26c from the first position to the second position during which the screw 26c dispenses liquid medicine from the cartridge 23 into a patient. As the screw 26c is moved from the first position to the second position, the annular contact plate 28c rotates therewith and relative to the first part 28b since the first set of pawls 252 of the annular contact plate 28c non-rotationally couple the annular contact plate 28c to the screw 26c during rotation of the screw 26c in the first rotational direction.

Upon the screw 26c moving to the second position, the screw 26c is either manually rotated or driven by the motor to rotate the screw 26c in the second rotational direction.

Since the sun gear 248 of the planetary gear set 244 is rotationally fixed to the screw 26c, the sun gear 248 rotates with the screw 26c in the second rotational direction. Rotation of the sun gear 248 in the second rotational direction causes the planet gears 250 to rotate along with the carrier plate 249. The surface features 255 of the carrier plate 249 engage the second set of pawls 253 of the annular contact plate 253 to cause the annular contact plate 28c to rotate therewith in the second rotational direction and at a reduced speed.

The various aspects and features disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described functional and/or operational aspects may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing unit" as used herein may refer to any of the foregoing structure or any other physical structure suitable for implementation of the described techniques. Also, the techniques could be fully implemented in one or more circuits or logic elements.

While several aspects of the present disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A medicine injection pen, comprising:
   a body;
   a drive member disposed within the body and configured to rotate in a first rotational direction relative to the body from a first position to a second position to dispense liquid medicine, the drive member configured to rotate in a second rotational direction from the second position to the first position to reset the drive member;

a rotary encoder including:
  a first part rotationally fixed relative to the body; and
  a second part configured to rotate with movement of the drive member to enable determination of an amount of liquid medicine dispensed based on a rotation of the second part relative to the first part; and
a gear set operably coupled to the second part of the rotary encoder, wherein the second part is configured to rotate freely relative to the gear set during movement of the drive member in the first rotational direction and to engage the gear set during movement of the drive member in the second rotational direction.

2. The medicine injection pen according to claim 1, wherein the gear set is a planetary gear set.

3. The medicine injection pen according to claim 2, wherein the planetary gear set includes a sun gear and a plurality of planet gears in meshing engagement with the sun gear, the second part configured to rotate about the sun gear with the planet gears in the second rotational direction.

4. The medicine injection pen according to claim 3, wherein the sun gear is configured to rotate with the drive member in the second rotational direction as the drive member moves from the second position to the first position.

5. The medicine injection pen according to claim 4, wherein the second part of the rotary encoder is configured to:
  rotate with the drive member in the first rotational direction at the same rate as the drive member as the drive member moves from the first position to the second position; and
  rotate with the planet gears via the sun gear in the second rotational direction at a lesser rate than the drive member as the drive member moves from the second position to the first position.

6. The medicine injection pen according to claim 5, wherein the drive member and the second part are configured to be rotated by a motor.

7. The medicine injection pen according to claim 6, further comprising a processor in communication with the motor, wherein the processor is configured to automatically control the motor to rotate the drive member in the second rotational direction upon the drive member moving to a predetermined position.

8. The medicine injection pen according to claim 1, wherein the drive member is a drive screw configured to rotate and translate relative to the body to urge a piston to slide to dispense the liquid medicine.

9. The medicine injection pen according to claim 8, wherein the rotary encoder is configured to sense rotation of the drive screw to enable determination of the amount of the liquid medicine dispensed.

10. The medicine injection pen according to claim 9, further comprising an electronics unit configured to determine the amount of the liquid medicine dispensed based on the sensed rotation.

11. The medicine injection pen according to claim 1, further comprising a cartridge housing releasably engageable with the body and configured to retain a medicine cartridge therein, the medicine cartridge configured to retain the liquid medicine therein and including a piston configured to slide within the medicine cartridge, wherein the drive member is configured to move relative to the body upon actuation thereof to urge the piston to slide within the medicine cartridge to thereby dispense at least some of the liquid medicine through a dispensing end of the medicine cartridge.

12. A medicine injection pen, comprising:
a body;
a drive member disposed within the body and configured to rotate in a first rotational direction relative to the body from a first position to a second position to dispense liquid medicine, the drive member configured to rotate in a second rotational direction from the second position to the first position to reset the drive member;
a rotary encoder including:
  a first part rotationally fixed relative to the body; and
  a second part configured to rotate with movement of the drive member to enable determination of an amount of liquid medicine dispensed based on a rotation of the second part relative to the first part; and
a gear set operably coupled to the second part of the rotary encoder, wherein the second part of the rotary encoder is configured to:
  rotate with the drive member in the first rotational direction at the same rate as the drive member as the drive member moves from the first position to the second position; and
  rotate with the gear set in the second rotational direction at a lesser rate than the drive member as the drive member moves from the second position to the first position.

13. The medicine injection pen according to claim 12, wherein the gear set is a planetary gear set.

14. The medicine injection pen according to claim 13, wherein the planetary gear set includes a sun gear and a plurality of planet gears in meshing engagement with the sun gear, the second part configured to rotate about the sun gear with the planet gears in the second rotational direction.

15. The medicine injection pen according to claim 14, wherein the sun gear is configured to rotate with the drive member in the second rotational direction as the drive member moves from the second position to the first position.

16. The medicine injection pen according to claim 12, wherein the drive member and the second part are configured to be rotated by a motor.

17. The medicine injection pen according to claim 16, further comprising a processor in communication with the motor, wherein the processor is configured to automatically control the motor to rotate the drive member in the second rotational direction upon the drive member moving to the second position.

18. The medicine injection pen according to claim 12, wherein the drive member is a drive screw configured to rotate and translate relative to the body to urge a piston to slide to dispense the liquid medicine.

19. The medicine injection pen according to claim 18, wherein the rotary encoder is configured to sense rotation of the drive screw to enable determination of the amount of the liquid medicine dispensed.

20. The medicine injection pen according to claim 19, further comprising an electronics unit configured to determine the amount of the liquid medicine dispensed based on the sensed rotation.

* * * * *